United States Patent
Van Der Walt et al.

(10) Patent No.: US 7,166,198 B2
(45) Date of Patent: Jan. 23, 2007

(54) TREATMENT OF FLUOROCARBON FEEDSTOCKS

(75) Inventors: Izak Jacobus Van Der Walt, Krugersdorp (ZA); Klaus Hintzer, Kastl (DE); Werner Schwertfeger, Alotting (DE); Gerald Lee Bauer, Hudson, WI (US)

(73) Assignees: South African Nuclear Energy Corporation Limited, District Brits (ZA); 3M Innovative Properties Company, Saint Paul, MN (US)

( * ) Notice: Subject to any disclaimer, the term of this patent is extended or adjusted under 35 U.S.C. 154(b) by 360 days.

(21) Appl. No.: 10/203,252

(22) PCT Filed: Feb. 9, 2001

(86) PCT No.: PCT/US01/04443

§ 371 (c)(1),
(2), (4) Date: Jun. 10, 2003

(87) PCT Pub. No.: WO01/58841

PCT Pub. Date: Aug. 16, 2001

(65) Prior Publication Data

US 2004/0094399 A1    May 20, 2004

Related U.S. Application Data

(60) Provisional application No. 60/181,508, filed on Feb. 10, 2000.

(51) Int. Cl.
    *B01J 19/08*    (2006.01)
(52) U.S. Cl. ............. 204/165; 219/121.59; 219/121.48

(58) Field of Classification Search ................ 204/165; 165/94
    See application file for complete search history.

(56) References Cited

U.S. PATENT DOCUMENTS

| 3,816,552 A | | 6/1974 | Hartwimmer ............ 260/648 F |
| 4,076,760 A | | 2/1978 | Hartwimmer ........ 260/653.1 R |
| 4,902,529 A | | 2/1990 | Rebhan et al. |
| 5,008,511 A | * | 4/1991 | Ross ..................... 219/121.48 |
| 5,611,896 A | * | 3/1997 | Swanepoel et al. ......... 204/169 |

FOREIGN PATENT DOCUMENTS

| DE | 195 18 208 | | 11/1995 |
| GB | 2066227 A | * | 7/1981 |

OTHER PUBLICATIONS

Partial English Translation of DE 195 18 208 dated Nov. 23, 1995.

* cited by examiner

*Primary Examiner*—Kishor Mayekar
(74) *Attorney, Agent, or Firm*—Ladas & Parry LLP

(57) ABSTRACT

A method of treating a fluorocarbon feedstock includes generating, in a high temperature zone, an electrical arc between at least one cathode and at least one anode, generating in the high temperature zone and by means of the electrical arc and a plasma gas, a thermal plasma having a tail flame, allowing a fluorocarbon feedstock comprising at least one fluorocarbon compound to form a reactive thermal mixture with the thermal plasma tail flame, with the fluorocarbon compound dissociating into at least one fluorocarbon precursor or reactive species having fewer carbon atoms than the fluorocarbon compound, and cooling the reactive thermal mixture to form, from the fluorocarbon precursor or reactive species, a fluorocarbon product.

14 Claims, 3 Drawing Sheets

TREATMENT OF FLUOROCARBON FEEDSTOCKS

This application is a 371 National Stage filing of PCT/US01/04443 on Feb. 10, 2001 which claims priority to U.S. Provisional Patent Application Ser. No. 60/181,508, filed on Feb. 10, 2000.

THIS INVENTION relates to the treatment of fluorocarbon feedstocks. It relates in particular to a method of treating a fluorocarbon feedstock, and to a quench probe for use in such a method.

According to a first aspect of the invention, there is provided a method of treating a fluorocarbon feedstock, which method includes generating, in a high temperature zone, an electrical arc between at least one cathode and at least one anode;

generating in the high temperature zone and by means of the electrical arc and a plasma gas, a thermal plasma having a tail flame;

allowing a fluorocarbon feedstock comprising at least one fluorocarbon compound to form a reactive thermal mixture with the thermal plasma tail flame, with the fluorocarbon compound dissociating into at least one fluorocarbon precursor or reactive species having fewer carbon atoms than the fluorocarbon compound; and cooling the reactive thermal mixture to form, from the fluorocarbon precursor or reactive species, a fluorocarbon product.

The plasma gas may, in one embodiment of the invention, be an inert gas such as argon, nitrogen, helium, or mixtures thereof. The inert gas thus serves only as a heat source and to sustain the plasma, and does not react with the fluorocarbon precursor or reactive species. However, in another embodiment of the invention, the plasma gas may be a reactive gas such as tetrafluoromethane ($CF_4$) which will thus, in the thermal plasma and hence in the reactive thermal mixture, dissociate into fluorine containing species and carbon containing species, which, on cooling of the reactive thermal mixture, will react with the fluorocarbon precursor or reactive species to form said fluorocarbon product. In yet another embodiment of the invention, the plasma gas may comprise a mixture of the inert gas and the reactive gas as hereinbefore described.

The fluorocarbon compound may, for example, have five or more carbon atoms. The fluorocarbon precursor or reactive species may then have less than five carbon atoms; the fluorocarbon product may then comprise at least one fluorocarbon compound also having less than five carbon atoms.

While the fluorocarbon feedstock may be a more-or-less pure feedstock comprising a single fluorocarbon compound, such as $C_6F_{14}$, it is envisaged that the flouracarbon feedstock will normally be a not directly usable fluorocarbon product comprising two or more of a range of fluorocarbon compounds such as $C_5F_{12}$, $C_6F_{14}$, $C_7F_{16}$, $C_8F_{18}$, $C_4F_8O$, $C_8F_{16}O$, $(C_3F_7)_3N$, $C_6F_{13}H$, $C_6F_{12}H_2$, or the like. Normally, one compound will be present in such a product as a dominant component, ie constitute the major proportion of such a product.

In one embodiment of the invention, the fluorocarbon feedstock may be in liquid form. The plasma gas may then be fed separately into the high temperature zone. However, in another embodiment of the invention, the fluorocarbon feedstock may be in vapour form. It may then be fed into the high temperature zone together with the plasma gas, or it may be introduced separately from the plasma gas, eg into the torch or plasmatron, with the plasma gas being fed into the high temperature zone.

In yet another embodiment of the invention, the fluorocarbon feedstock may initially be in liquid form, with it being vaporized before being fed into the high temperature zone together with the plasma gas or introduced separately, as hereinbefore described. The vaporization of the feedstock may be effected by passing the liquid feedstock through a bubbler at a suitable temperature, or by means of any other suitable vapour generator.

Typical products which may be obtained are tetrafluoromethane ($CF_4$), tetrafluoroethylene ($C_2F_4$), hexafluoroethane ($C_2F_6$), hexafluoropropylene ($C_3F_6$), fluorobutylene ($C_4F_6$), cyclic octafluorobutane (c-$C_4F_8$), decafluorobutane ($C_4F_{10}$), octafluoropropane ($C_3F_8$) and other $C_xF_y$ chains where x and y are integers.

The cathode and the anode, ie the electrodes, may thus be those of a plasma torch or plasmatron driven by a power supply, with the plasma tail flame forming at the outlet of the torch or plasmatron.

The generation of the thermal plasma, the dissociation of the fluorocarbon compounds, and the cooling of the reactive thermal mixture may thus be effected in a plasma reactor, to which the plasma torch or plasmatron is mounted, and which has a reaction chamber. The plasma torch or plasmatron may, in particular, be located at an upper end of the reaction chamber. The plasmatron will then be downwardly burning, ie the plasma tail flame will travel downwardly into the reaction chamber.

In principle, any suitable plasmatron or plasma torch may be used. For example, the plasmatron may comprise a single water cooled hot cathode and a battery of up to three water cooled anodes, with the arc thus passing between the cathode and anodes. The cathode may include a suitable insert such as a tungsten or graphite insert.

The high temperature zone may be provided by a region in and around, and in the immediate vicinity of, the arc of the plasma torch or plasmatron, ie the arc between the electrodes, and/or by a region immediately below the plasma torch or plasmatron inside an expansion portion or area of the reaction chamber of the reactor.

The expansion of the thermal plasma tail flame, the dissociation of the fluorocarbon compound, and the cooling of the reactive thermal mixture thus takes place in the reaction chamber, with the thermal plasma tail flame expansion and the fluorocarbon compound dissociation being effected in a first zone of the reaction chamber, and the reactive thermal mixture cooling being effected in a second zone of the reaction chamber. The plasmatron will thus be mounted to the reactor adjacent the first zone of the reaction chamber so that the plasma can be generated and expanded in the first zone of the reaction chamber.

The feeding of the plasma gas and, where applicable, the feedstock in vapour form, into the high temperature zone may thus be effected by injecting the gas between the electrodes in such a manner that the thermal plasma forms a vortex in the plasma torch or plasmatron. Additional plasma gas may be introduced between consecutive anodes, to sustain the vortex through the first zone of the reaction chamber.

The feedstock, when in liquid form, may be introduced into the torch or plasmatron, ie into the arc between the electrodes, or into the plasma tail flame. When the liquid feedstock is introduced into the plasma tail flame, it may be fed either tangentially into the plasma tail flame, or axially, countercurrently to the plasma tail flame, or at any other desired angle; however, it is believed that by feeding the feedstock axially into the plasma tail flame countercurrently to the direction of travel of the plasma tail flame, ie axially upwardly into the plasma tail flame, particularly good results will be obtained since all liquid feedstock can then be vaporized by the tail flame before entering the plasma in a wholly gas phase.

The feeding of the liquid feedstock into the tail flame is normally by means of injection, ie through an injection nozzle. On start-up, and in order to protect, ie cool, the nozzle, liquid feedstock is preferably injected just prior to initiation of the plasma. Otherwise, the feeding of the feedstock into the thermal plasma is thus effected after the plasma has been initiated.

Additionally, the feedstock may be introduced through a single entry or injection point or nozzle, or through multiple injection or entry points or nozzles which, it is believed, will increase the amount of feedstock that can be vaporized by the plasma tail flame.

The cooling of the second zone of the reaction chamber may be effected by means of a quench probe, which may be a self-cleaning quench probe. The self cleaning quench probe may comprise an outer cylindrical component mounted to the reactor, providing a central passageway and adapted to cool the hot gas or reactive thermal mixture passing through the passageway; a plurality of circumferentially spaced elongate teeth or scrapers protruding inwardly from the outer component into the passageway; an inner cylindrical component located with clearance inside the outer component, with the inner component also adapted to cool the hot gas or reactive thermal mixture passing along the peripheral gap between the components; a plurality of circumferentially spaced elongate teeth or scrapers protruding outwardly from the inner component into the passageway, with these teeth or scrapers being staggered with respect to the teeth or scrapers on the outer component; and drive means for driving the one cylindrical component to oscillate relative to the other cylindrical component. The drive means may, for example, comprise a spring loaded piston driven arm.

Instead, however, any other suitable quenching means can be used such as rapid expansion of the product gas, gas quenching by means of another gas which is cold, or the like.

The reaction chamber may be operated under pressures ranging from near vacuum to elevated pressures, depending on the specific reaction, ie depending on the feedstock and the desired fluorocarbon compound to be formed. Evacuation may be effected through the quench probe.

According to a second aspect of the invention, there is provided a quench probe which comprises
- an outer cylindrical component providing a central passageway and adapted to cool a hot gas passing through the passageway;
- a plurality of circumferentially spaced elongate teeth or scrapers protruding inwardly from the outer component into the passageway;
- an inner cylindrical component located with clearance inside the outer component, with the inner component adapted to cool the hot gas passing along the peripheral gap between the components;
- a plurality of circumferentially spaced elongate teeth or scrapers protruding outwardly from the inner component into the passageway, with these teeth or scrapers being staggered with respect to the teeth or scrapers on the outer component; and
- drive means for driving the one cylindrical component to oscillate relative to the other cylindrical component.

The inner component may be located centrally or concentrically within the outer component. The same number of teeth or scrapers may be provided on the inner and outer components. The teeth or scrapers may be spaced equidistantly apart on their components. The teeth or scrapers may extend parallel to one another.

The components may be hollow and/or may be provided with passages to permit a cooling fluid, such as water, to pass through them in order to cool or quench the hot gas.

The drive means may, as also hereinbefore described, comprise a spring loaded piston driven arm attached to one of the cylindrical components.

Due to the oscillation of the one component relative to the other, removal of solidified or sublimated material deposited on the surfaces thereof, on passage of the gas through the annular gap between the components, is achieved.

The quench probe is particularly suited for use in a plasma reactor as hereinbefore described; however, it is not limited only to such use. Normally, the outer component will be fixed to the reactor, with the inner component oscillating relative to the outer component.

The invention will now be described by way of example, with reference to the accompanying diagrammatic drawings.

IN THE DRAWINGS

Figure 1:
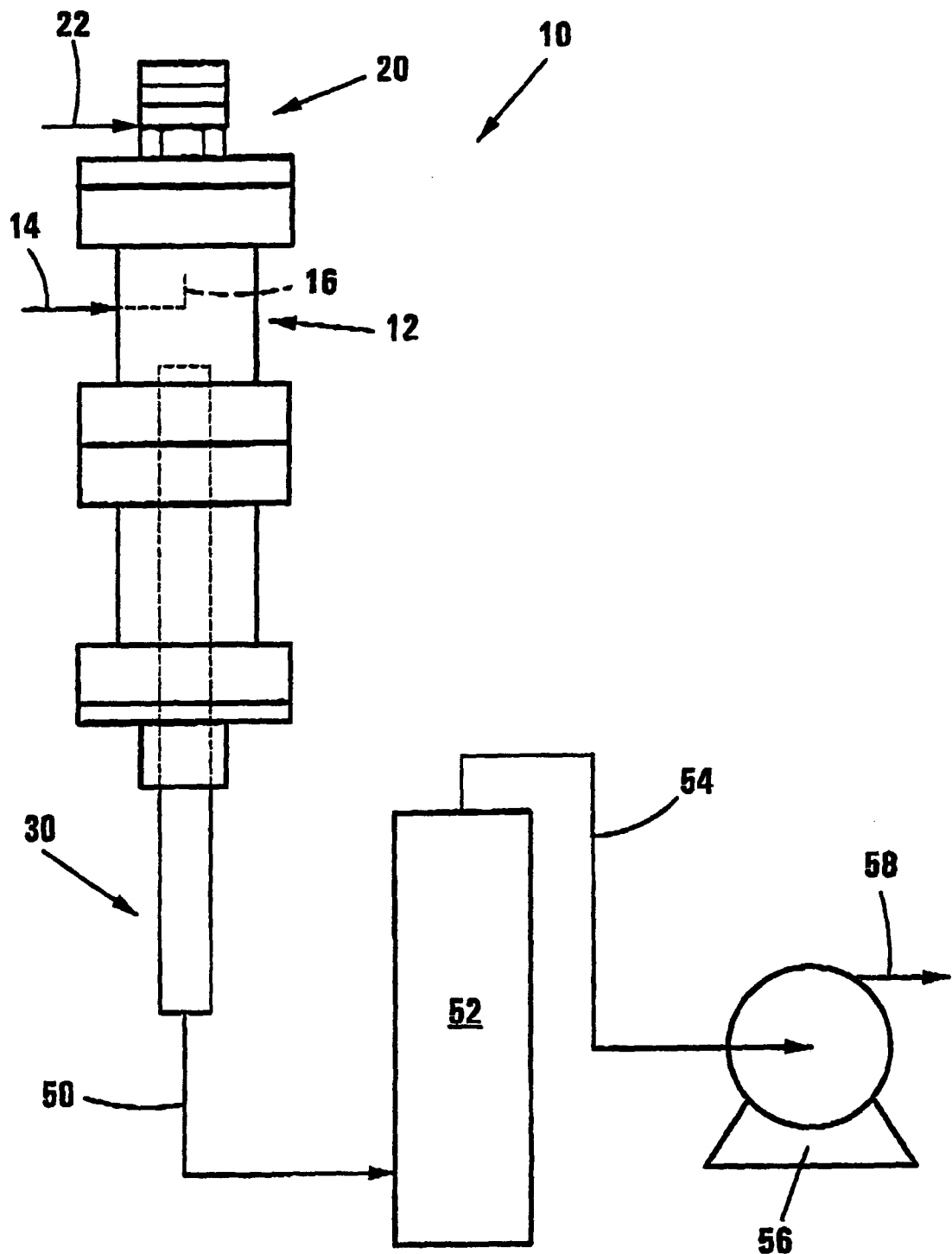
FIG. 1 shows, in simplified flow diagram form, an installation for carrying out a method of treating a fluorocarbon feedstock, in accordance with one embodiment of the invention.
Figure 2:
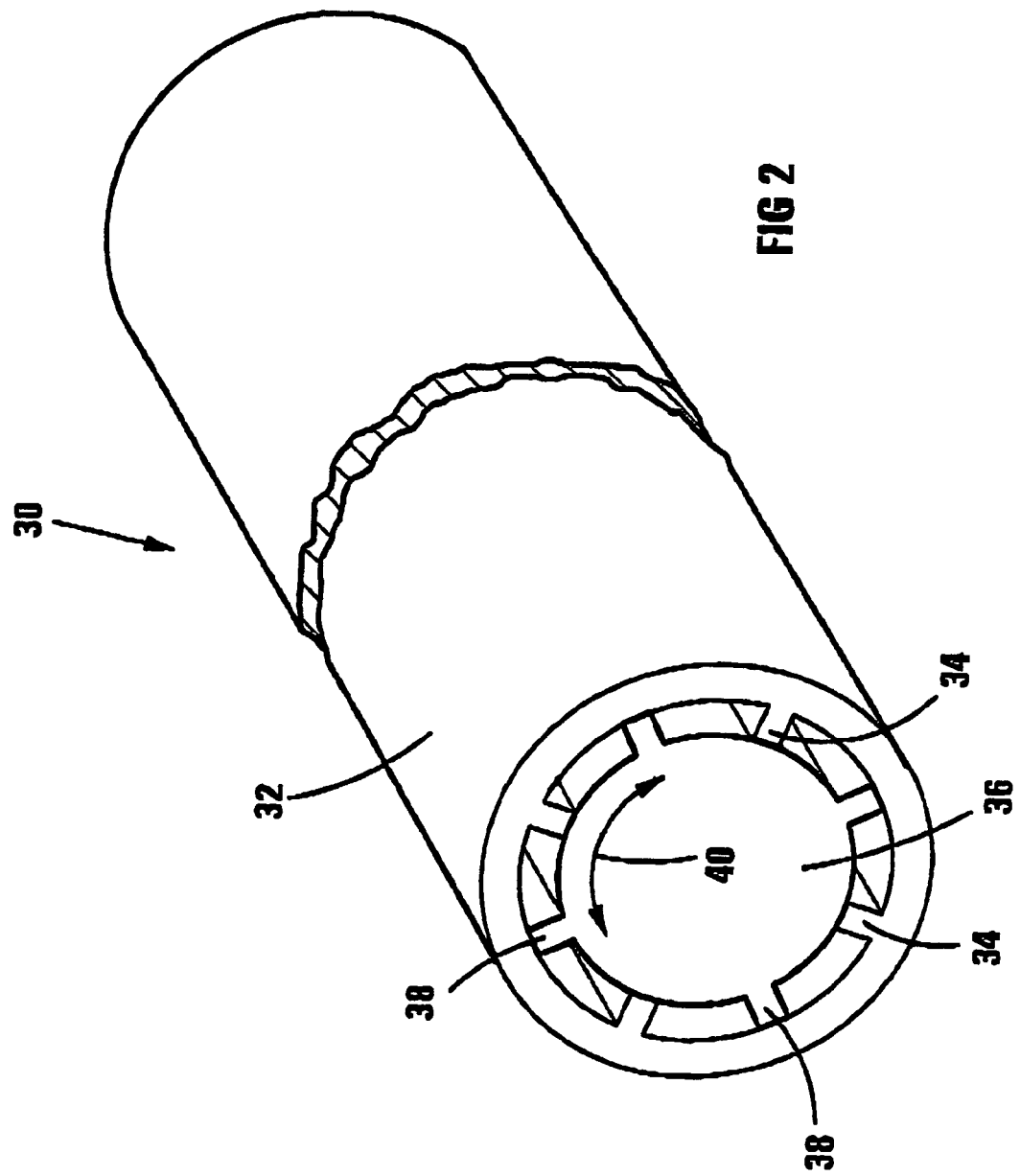
FIG. 2 shows a three-dimensional view of the quench probe of the reactor of FIG. 1.

Referring to FIGS. 1 and 2, reference numeral 10 generally indicates an installation for carrying out a method of treating a fluorocarbon feedstock, according to one embodiment of the invention.

The installation 10 includes a plasma reactor, generally indicated by reference numeral 12. The reactor 12 is of elongate form, and is arranged vertically. The reactor is double-walled (not shown) and water cooled (not shown) with sampling holes, (not shown) spaced at various heights, provided in the side of the reactor. The sampling holes are used to characterize the plasma which forms at the top of the reactor for different gases, and to obtain temperature profiles, flow patterns and gas composition data from inside the reactor while the plasma is burning.

A feedstock feed line 14 leads into the side of the reactor 12 and is fitted with an upwardly directed injection nozzle 16.

The installation 10 includes a plasma torch or plasmatron, generally indicated by reference numeral 20, mounted to the upper end of the reactor 12. The plasma torch or plasmatron 20 comprises a water cooled hot cathode (not shown) and a battery of up to three water cooled anodes (not shown). The hot cathode includes a tungsten or graphite insert (not shown). A plasma gas injection flow line 22 leads into the plasma torch 20. In use, plasma gas passes through the flow line 22 and is injected into the torch 20 between the cathode and anodes in such a manner that the resultant gas stream forms a vortex stabilized plasma.

The installation 10 also includes a self-cleaning quench probe, generally indicated by reference numeral 30, protruding into the lower end of the reactor 12. The self-cleaning quench probe 30 comprises an elongate watercooled cylindrical outer component 32, which is fixed to the reactor 12.

The outer component 32 thus has a central passageway into which protrudes equally spaced elongate radially inwardly protruding teeth or scrapers 34. Inside the passageway of the outer component 32 is located, with peripheral clearance, an elongate watercooled inner cylindrical component 36. Equally spaced elongate radially outwardly protruding teeth or scrapers 38 are provided on the inner component 36, with the teeth 38 being spaced circumferentially from the teeth 34. The teeth 34, 38 may extend the full length of the components 32, 36, and the components 32 and 36 are of substantially the same length. The inner component 36 is provided with drive means (not shown), such as a spring loaded piston driven arm, for driving it to oscillate relative to the outer component 32, as indicated by the arrow 40. Removal of solid contaminants from the components 32, 36 is thus achieved by means of the oscillating teeth 34, 38. By moving the quench probe 30 up and down, the effective length of the reactor can be increased or decreased, thereby to optimize the reactor length.

The quench probe 30 is thus a double annular water cooled probe designed to cool the plasma gas or reactive thermal mixture that forms inside the reactor 12 as hereinafter described, down to below 200° C. at a rate of about $10^5$° C./second. The probe is self cleaning to prevent blockages thereof since solidified or sublimated material forms on the surfaces of the probe in use.

A flow line 50 leads from the lower end of the quench probe 30 to a filter 52, with a flow line 54 leading from the filter 52 to a vacuum pump 56. A product withdrawal line 58 leads from the pump discharge. By means of the vacuum pump 56, a vacuum is thus drawn on the reactor 12.

In use, on feeding a plasma gas, such as argon, into the plasma torch 20 through the flow line 22, a plasma is generated between the cathode and anodes, and at the upper end of a reaction chamber (not shown) of the reactor 12. The plasma burns downwardly, and a downwardly moving and transversely expanding plasma tail flame is formed. The feedstock injection nozzle 16 is located in the tail flame. A liquid feedstock comprising at least one fluorocarbon compound having five or more carbon atoms, is injected through the nozzle 16, ie in a direction 180° counter to the direction of movement of the plasma tail flame, it is vaporized so that the feedstock is in wholly gaseous form when it reacts with the plasma gas. The fluorocarbon compound of the feedstock dissociates into fluorocarbon precursors or reactive species. This occurs in an upper zone of the reaction chamber provided by the reactor 12. As the thermal reactive mixture move downwardly into a lower zone of the reaction chamber, ie the zone in which the quench probe 30 is located, the reactive thermal mixture is cooled down thereby forming the plasma product containing at least one more desired fluorocarbon compound having less than five carbon atoms.

Figure 3:
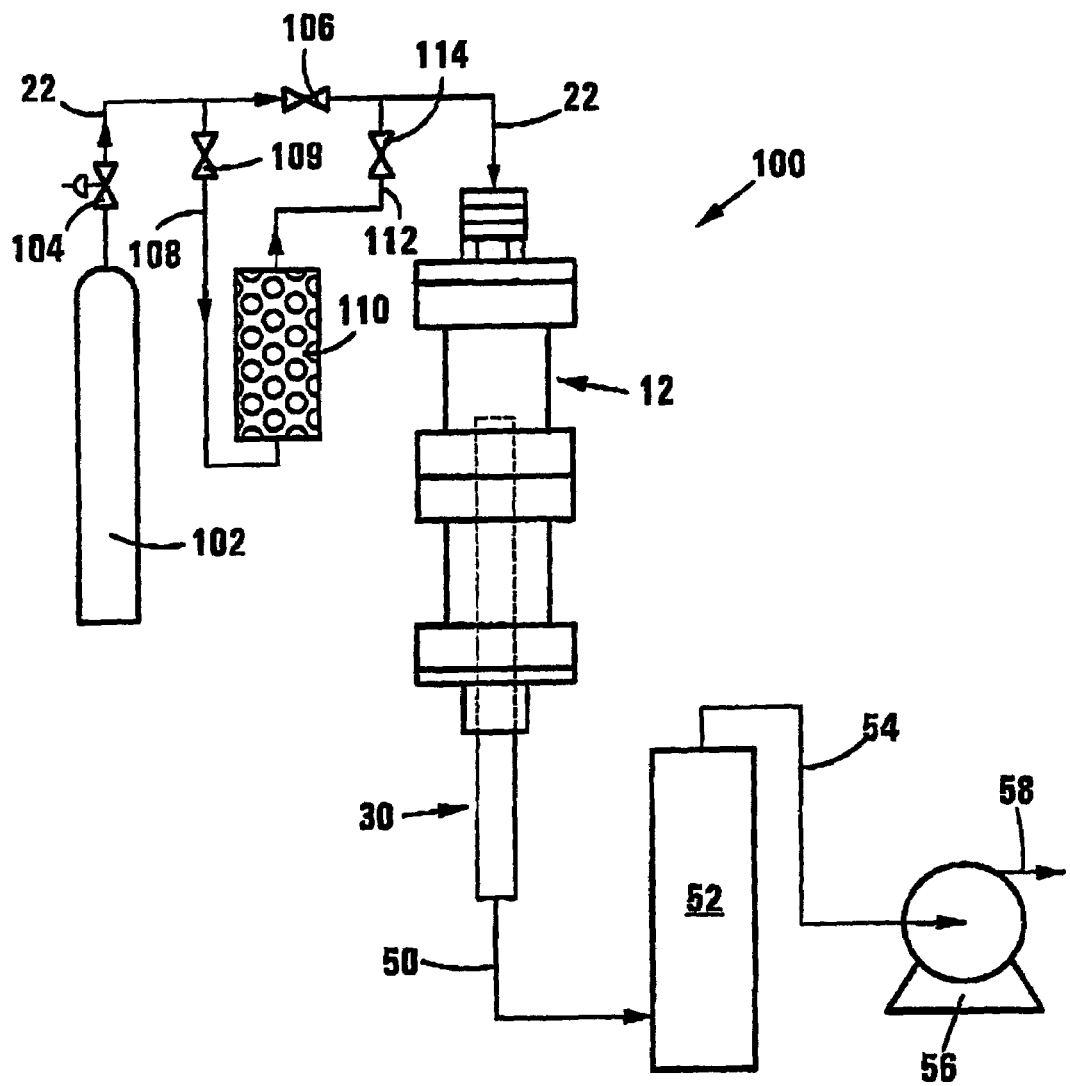
FIG. 3 shows, in simplified flow diagram form, an installation for carrying out a method of treating a fluorocarbon feedstock, in accordance with another embodiment of the invention.

Referring to FIG. 3, reference numeral 100 generally indicates an installation for carrying out a method of treating a fluorocarbon feedstock, according to another embodiment of the invention.

Parts of the installation 100 which are the same or similar to those of the installation 10 hereinbefore described with reference to FIGS. 1 and 2, are indicated with the same reference numerals.

The installation 100 includes a supply cylinder 102 containing a supply of $CF_4$ plasma gas. The plasma gas supply line 22, fitted with a control valve 104 and a shut-off valve 106, leads from the cylinder 102. A line 108 leads from the line 22, upstream of the valve 106, into a bubbler 110. The line 108 is fitted with a valve 109. A line 112 leads from the bubbler 110 and is fitted with a valve 114. The line 112 leads into the line 22 downstream of the valve 106.

In the installation 100, the feedstock is first vaporized in the bubbler 110, and then fed, as a vapor and together with the $CF_4$ plasma gas, between the cathode and anode. The bubbler 110 thus contains the feedstock in liquid form. The $CF_4$ plasma gas bubbles through the liquid feedstock, with the $CF_4$ plasma gas thus becoming saturated with the feedstock in vapour form before entering the plasma reactor 12.

In the specific Examples hereinafter discussed, a 30 kw plasma torch or plasmatron was used. A plasma gas flow rate of about 3 kg/hour was used. Before commencing the tests or examples, the system was evacuated to about 10 kPa, and flushed with argon. The plasma was initiated by a high voltage starter (not shown) and maintained by a 30 kW power supply. After the argon plasma initiation had been completed, a switch-over to the desired plasma gas was done. It will, however, be appreciated that on other reactor systems, the plasmatron can be initiated directly on the desired plasma gas, depending on the design of the plasmatron.

EXAMPLE 1

The installation 10, operating with an argon plasma, was used. The feedstock comprised liquid by-product consisting of $C_6F_{14}$–$C_{10}F_{22}$ fluorocarbons, with the $C_6F_{14}$ being present in excess of 90% (molar basis). It was found that after three hours, the reactor was still relatively clean, with only a thin carbon layer deposited on the cold surfaces of the reactor.

The results obtained are set out in Tables 1 and 2.

EXAMPLE 2

The same installation as in Example 1, was used. A $CF_4$ plasma torch and $CF_4$ plasma gas were used in this example. The results of this test compared well to those of Example 1, as indicated in Tables 1 and 2. The only substantial difference between Examples 1 and 2 is that a final separation of the plasma gases is required in Example 1, since argon used for the plasma in Example 1, is inert and does not take part in the reaction. The excess argon thus needs to be separated out, as an additional step.

TABLE 1

| Results | | |
|---|---|---|
| | Example 1 Ar plasma gas | Example 2 $CF_4$ plasma gas |
| Torch efficiency (%) | 44 | 77 |
| Energy In (kW) | 7.5 | 25.8 |
| Energy Out (kW) | 9.7 | 25.7 |
| Enthalpy below torch (kWh/kg) | 1.1 | 6.6 |
| Run time (min) | 182 | 188 |
| Liquid fluorocarbon feed rate (kg/h) | 1.87 | 0.91 |
| Mass feedstock fed (kg) | 5.67 | 2.85 |
| Mass deposit relative to feed (kg/kg) | 0.00457 | 0.0147 |

As can be seen from Table 1, the feed mass flow rate of Example 1 is more than double that in Example 2. However, the deposits in Example 1 were substantially less compared to those of Example 2. The argon assisted conversion of Example 1 is more efficient on throughput of material for the setup and system configuration as indicated in FIG. 1.

TABLE 2

Analytical Results

| Plasma products | Example 1<br>Ar plasma gas | Example 2<br>$CF_4$ plasma gas |
| --- | --- | --- |
| Air/Ar (%) | — | — |
| $CF_4$ (%) | 4.4 | 15.7 |
| $C_2F_6$ (%) | 10.6 | 8.7 |
| $C_2F_4$ (%) | 43.7 | 46.8 |
| $C_3F_8$ (%) | 16.5 | 15.6 |
| $C_3F_6$ (%) | 14.6 | 8 |
| Other | 10.2 | 5.2 |

In Table 2, the concentrations of the product compounds as analyzed by gas chromatography have been normalized with respect to the resulting plasma product constituents, in order to simplify the comparison between the different examples. This eliminates the distortion of the nearly 90% argon/air in Example 1, and 10% air in Example 2. However, it must be recognized that the excessive value of argon in the first run still has to be recovered from the product stream as well as the air in both cases.

The reactor configuration of FIG. 1 described hereinbefore with the specific process conditions as also described hereinbefore, is set up for the manufacture of TFE ($C_2F_4$). When it is desired to maximize the production of any other fluorocarbon products having less than 5 carbon atoms, it will be necessary to change the reactor conditions to obtain suitable yields of that specific product.

EXAMPLE 3

In this example, a series of different fluorocarbon liquids as indicated in Table 3, were converted into useful products such as tetrafluoroethylene (TFE), hexafluoropropylene (HFP) and cyclic $C_4F_8$, with the emphasis on TFE. The installation of FIG. 3 was used. Thus, the feedstock was introduced, as a vapor, into the plasmatron between the cathode and anode. This was achieved by means of the bubbler 110 through which the $CF_4$ plasma gas was bubbled. The vapor pressures of the various feedstocks as well as the bubbler temperature determined the evaporation and hence the flow rate of the feedstock being fed into the plasma.

The plasma reactor 12 was run under normal start-up conditions for approximately 5 minutes after which the $CF_4$ was routed through the liquid feedstock in the bubbler at a bubbler pressure of 130 kPa (abs). The $CF_4$ saturated with feedstock vapor was fed into the plasma torch, which was maintained at about 10 kPa (abs). The plasma current was then adjusted to achieve the desired enthalpy. Almost all the runs started on an enthalpy of about 6,4 kWh/kg of plasma gas and after an hour it was lowered to about 4 kWh/kg of plasma gas. The feedstock feed rate, plasmatron potential and current, feedstock temperature, cooling water temperature and reactor pressures were constantly measured and logged against time. GC samples were taken under stable equilibrium conditions to represent each run.

Table 3 shows the operating conditions for the different runs arranged according to decreasing molecular weight (mw) of the liquid feedstock. Some run times were shorter than others, eg the runs with $C_5$ and $C_6$ liquid feedstocks, because of their higher evaporation rate and the limited bubbler capacity. In some cases the temperature of the bubbler was varied to investigate the effect on yield of higher evaporation and hence feed rate into the plasma.

Table 4 shows the relative product yields along with the plasma enthalpies at two levels, namely, at the outlet of the torch and directly upstream of the quench probe. In general it is observed that for the same system conditions (Volts, Amperes, $CF_4$ mass flow, bubbler temperature) the enthalpy decreases as the molecular weight ('mw') of the liquid decreases. This is due to the increased amount of vapor present in the gas stream for the higher vapor pressure samples, which had the effect of increasing the total mass flow through the torch. The torch efficiency accounts for the energy that is lost inside the torch due to radiation. In the analytical results only the most prominent products are mentioned. Other products such as $C_3F_8$, $C_4F_6$, $C_4F_{10}$, etc. only make up about 1–2% of the total product gases. Generally speaking, at bubbler temperatures from ambient conditions up to about 40° C. the lower molecular weight liquids ($C_5F_{12}$ and $C_6F_{14}$) produced the best TFE yields. The main reason for this is their higher evaporation (feed) rate for the same $CF_4$ plasma-gas feed rate.

Table 5 summarizes the mass balance calculated for each run. The outlet flow from the process was not measured. However, since there were no traces of condensable materials in the product, the assumption was made that 100% of the feedstock had been converted into gaseous products. On this basis the $CF_4$ consumption was calculated as the difference between $CF_4$ flow rate in and out. The carbon balance column, however, indicates that in almost all runs additional carbon had been added, probably from the graphite lining inside the reactor. This phenomenon is more pronounced at high enthalpies than at lower values.

An important aspect of the conversion process is the $CF_4$ consumption. In all but the last run, $CF_4$ was consumed. Also, at high enthalpies more $CF_4$ was consumed than at low enthalpies. Conversely, in run 7 ($C_5F_{12}$) the $CF_4$ content in the product gases was higher than in the initial plasma feed. A possible explanation is that $CF_4$ is formed as an intermediate in the initial cracking process for at least some of these liquids and that the rate of formation of $CF_4$ in this instance (short carbon chain length) exceeds the consumption.

Superficially, high enthalpy appears to be advantageous for TFE production, a phenomenon which is more accentuated with the higher molecular weight liquids. However, close inspection reveals that this also correlates with high $CF_4$ consumption as well as with carbon utilization from the erosion of the graphite lining. These findings therefore, rather illustrate that energy is being wasted in converting valuable plasma gas ($CF_4$) into TFE instead of converting the liquid feed. Another disadvantage of high enthalpy is the phenomenon of anode erosion in the plasmatron, as discussed hereinafter.

In contrast, the low enthalpy sections of the runs (first row in each run, Table 4) clearly illustrate that the TFE yield rate is substantially proportional to the liquid fluorocarbon feed rate. Any discrepancies may be accounted for by the variation in $CF_4$ consumption rates. Furthermore, the $CF_4$ consumption was relatively low at about 0.5 kg/h across the board, except in run 7 as discussed above, where surprisingly it was negative. Since $CF_4$ is a high value commodity utilized here as the plasma gas, ie the heat source, ideally it should not participate in the production of the desired gases, but rather be recirculated through the process cycle. Thus the finding in run 7 was not only unexpected but highly encouraging, since this means that low molecular weight fluorocarbon liquids such as $C_5F_{12}$ can be utilized as an additional source of $CF_4$ and, fed in the right proportion, may be introduced in any production run to establish a self sustaining fluorocarbon materials conversion plasma reactor, saving input costs of raw materials.

The TFE production rate seems to be proportional to the liquid fluorocarbon feed rate, irrespective of the nature (molecular weight) of the liquid, and since the feedstock (vapor) feed rate evidently varies proportionally to the vapor pressure of the particular feedstock to be converted, it is assumed that the production rates from higher molecular weight feedstocks could be raised by raising the temperature of the liquid feedstock in the bubbler chamber above the upper limit of 40° C. in the present runs. Subsequent runs at such higher temperatures and at prolonged times (not shown) have been encouraging.

Visual inspection of the reactor after run times of up to 4 hours showed no significant residue anywhere in the system. The graphite lining inside the reactor seems to have served as a consumable carbon source, but it is highly likely that the primary erosion was caused by mechanical wear due to the high velocity gas. It is therefore possible in prolonged runs that the erosion of the lining may taper off to a point where the graphite will remain constant in mass.

No blockages occurred in the quench probe or in the filters during any of the runs, which generally occurred when raw carbon was fed into such a reactor (runs not shown). Similarly, during a number of preliminary runs (also not shown) a build up of carbon from the carbon inserts in the cathode caused an electrical short between the cathode and anode. This was more pronounced in longer runs and particularly with high enthalpy values. During the present runs, however, no significant build up or any form of deposit was observed in the plasmatron.

It is apparent that the vapor phase introduction of liquid feedstocks into the plasma is advantageous and yields relatively good results with low maintenance. Moreover, the relative yields of the products may be controlled by appropriately adjusting either the process parameters or the feed mix or both.

TABLE 3

Operating Conditions

| Run Number | Liquid Fluoro-carbon sample Identification | Total feed rate (kg/h) $CF_4$ | Total feed rate (kg/h) Liquid Feedstock | Liquid Feed Temp (° C.) | Liquid Feed Vapor P (kPa) | Reactor Pressure (kPa abs) | Plasma Input Power Voltage (V) | Plasma Input Power Current (A) | Run time (minutes) Overall | Run time (minutes) Liquid Feedstock |
|---|---|---|---|---|---|---|---|---|---|---|
| 1 | FC 3283 | 3.0 | 0.15 | 25 | 1.1 | 10.7 | 114 | 150 | 175 | 157 |
|   | $(C_3F_7)_3N$ | 3.0 | 0.15 | 25 | 1.1 | 11.0 | 114 | 250 | 175 | 157 |
| 2 | FC 3255 | 3.0 | 0.44 | 25 | 5.6 | 11.3 | 125 | 140 | 138 | 130 |
|   | $C_8F_{18}$ | 3.0 | 0.44 | 25 | 5.6 | 11.3 | 114 | 251 | 138 | 130 |
| 3 | FC 74 | 3.0 | 0.39 | 25 | 6.1 | 10.5 | 125 | 140 | 131 | 130 |
|   | 60% $C_8F_{18}$ | 3.0 | 0.39 | 25 | 6.1 | 10.5 | 111 | 250 | 131 | 130 |
| 4 | FC 6003 | 3.0 | 0.45 | 25 | 5.6 | 10.2 | 125 | 140 | 132 | 126 |
|   | $C_8F_{18}$ + x* | 3.0 | 0.45 | 25 | 5.6 | 10.8 | 110 | 250 | 132 | 126 |
| 5 | PF 5070 | 4.9 | 1.7 | 33 | 14 | 12.9 | 155 | 145 | 97 | 89 |
|   | $C_7F_{16}$ | 3.0 | 1.5 | 28 | 13 | 12.7 | 136 | 146 | 68 | 64 |
| 6 | PF 5060 | 3.9 | 2.4 | 18 | 22 | 11.0 | 143 | 145 | 84 | 77 |
|   | $C_6F_{14}$ | 4.0 | 2.8 | 31 | 38 | 12.5 | 163 | 145 | 84 | 77 |
| 7 | PF 5050 | 3.0 | 4.4 | 17 | 64 | 12.8 | 166 | 145 | 64 | 63 |
|   | $C_5F_{12}$ | 2.0 | 4.0 | 15 | 57 | 9.0 | 127 | 250 | 64 | 63 |
|   |   | 1.0 | 4.0 | 20 | 70 | 8.3 | 120 | 250 | 64 | 63 |

*x = other components, possibly other fluorocarbons

TABLE 4

Product Gas and Plasma Analysis

| Run Number | Liquid Fluoro-carbon sample Identification | Energy in (kW) | Torch efficiency*** (%) | Enthalpies (kWh/kg) Torch | Enthalpies (kWh/kg) Quench | Plasma products (vol %) $CF_4$ *88 | Plasma products (vol %) $C_2F_6$ *138 | Plasma products (vol %) $C_2F_4$ *100 | Plasma products (vol %) $C_3F_6$ *150 |
|---|---|---|---|---|---|---|---|---|---|
| 1 | FC 3283 | 17.1 | 71 | 3.8 | 1.2 | 77.5 | 3.9 | 13.5 | 0.6 |
|   | $(C_3F_7)_3N$ | 28.5 | 72 | 6.5 | 1.8 | 60.8 | 6.7 | 28.2 | 2.3 |
| 2 | FC 3255 | 17.5 | 70 | 3.5 | 0.5 | 86.1 | 3.3 | 10.8 | 0.0 |
|   | $C_8F_{18}$ | 28.5 | 71 | 5.9 | 1.8 | 54.2 | 7.8 | 33.8 | 2.8 |
| 3 | FC 74 | 17.5 | 74 | 3.8 | 1.4 | 75.7 | 4.2 | 15.4 | 0.8 |
|   | 60% $C_8F_{18}$ | 27.7 | 74 | 6.0 | 2.9 | 76.8 | 4.8 | 16.1 | 1.1 |
| 4 | FC 6003 | 17.5 | 71 | 3.6 | 0.4 | 78.7 | 4.7 | 14.8 | 0.7 |
|   | $C_8F_{18}$ + x** | 27.5 | 74 | 5.9 | 3.0 | 58.3 | 7.7 | 30.0 | 2.1 |
| 5 | PF 5070 | 22.4 | 85 | 2.7 | 1.6 | 69.0 | 6.0 | 24.0 | 1.0 |
|   | $C_7F_{16}$ | 19.8 | 80 | 3.5 | 1.9 | 59.0 | 12.0 | 28.0 | 0.0 |
| 6 | PF 5060 | 20.7 | 82 | 2.7 | 1.6 | 57.0 | 5.2 | 32.0 | 5.8 |
|   | $C_6F_{14}$ | 23.6 | 85 | 2.9 | 1.8 | 56.0 | 6.0 | 34.0 | 4.0 |
| 7 | PF 5050 | 24.1 | 81 | 2.6 | 1.3 | 53.0 | 0.0 | 47.0 | 0.0 |

TABLE 4-continued

Product Gas and Plasma Analysis

| Run Number | Liquid Fluoro-carbon sample Identification | Energy in (kW) | Torch efficiency*** (%) | Enthalpies (kWh/kg) Torch | Enthalpies (kWh/kg) Quench | Plasma products (vol %) $CF_4$ *88 | Plasma products (vol %) $C_2F_6$ *138 | Plasma products (vol %) $C_2F_4$ *100 | Plasma products (vol %) $C_3F_6$ *150 |
|---|---|---|---|---|---|---|---|---|---|
| | $C_5F_{12}$ | 31.7 | 84 | 4.4 | 2.0 | 39.0 | 11.0 | 50.0 | 0.0 |
| | | 30.0 | 79 | 4.7 | 2.3 | 29.0 | 11.0 | 54.0 | 0.0 |

*Product component molecular mass in kg/mole
**x = other components, possibly other fluorocarbons
***Calculated calorimetrically from the cooling water circuits

TABLE 5

Mass flow balance

| | | Input | | | | Products | | | | % Error | |
|---|---|---|---|---|---|---|---|---|---|---|---|
| | | Feed flow rate (kg/h) | Feed flow rate (kg/h) | Mole mass of Liquid Feedstock (kg/kmole) | $CF_4$ Consumption (kg/h) | $CF_4$ flow rate (kg/h) | $C_2F_8$ flow rate (kg/h) | $C_2F_4$ flow rate (kg/h) | $C_3F_6$ flow rate (kg/h) | C— balance (%) | F— balance (%) |
| Run Number | Liquid Fluoro-carbon sample Identification | $CF_4$ | Liquid Feedstock | | | | | | | | |
| 1 | FC 3283 | 3.0 | 0.15 | 521 | 0.56 | 2.44 | 0.19 | 0.48 | 0.03 | −11 | 2 |
|   | $(C_3F_7)_3N$ | 3.0 | 0.15 | | 1.21 | 1.79 | 0.31 | 0.94 | 0.12 | −25 | 4 |
| 2 | FC 3255 | 3.0 | 0.45 | 438 | 0.13 | 2.87 | 0.17 | 0.41 | 0.00 | −2 | 0 |
|   | $C_8F_{18}$ | 3.0 | 0.45 | | 1.29 | 1.71 | 0.38 | 1.21 | 0.15 | −23 | 4 |
| 3 | FC 74 | 3.0 | 0.40 | 438 | 0.46 | 2.54 | 0.22 | 0.59 | 0.05 | −8 | 1 |
|   | 60% $C_8F_{18}$ | 3.0 | 0.40 | | 0.50 | 2.50 | 0.24 | 0.60 | 0.06 | −9 | 2 |
| 4 | FC 6003 | 3.0 | 0.36 | 438 | 0.46 | 2.54 | 0.24 | 0.54 | 0.04 | −8 | 1 |
|   | $C_8F_{18} + x^*$ | 3.0 | 0.36 | | 1.19 | 1.81 | 0.38 | 1.06 | 0.11 | −22 | 4 |
| 5 | PF 5070 | 4.9 | 1.70 | 388 | 0.66 | 4.24 | 0.58 | 1.68 | 0.10 | −7 | 1 |
|   | $C_7F_{16}$ | 3.0 | 1.53 | | 0.56 | 2.44 | 0.78 | 1.31 | 0.00 | −6 | 1 |
| 6 | PF 5060 | 3.7 | 2.40 | 338 | 0.58 | 3.12 | 0.45 | 1.99 | 0.54 | −8 | 2 |
|   | $C_6F_{14}$ | 4.0 | 2.86 | | 0.53 | 3.47 | 0.58 | 2.39 | 0.42 | −9 | 2 |
| 7 | PF 5050 | 3.0 | 4.40 | 288 | −0.69 | 3.69 | 0.00 | 3.71 | 0.00 | −5 | 1 |
|   | $C_5F_{12}$ | 2.0 | 4.00 | | 0.38 | 1.62 | 0.96 | 3.42 | 0.00 | −9 | 2 |
|   | | 1.0 | 4.00 | | −0.72 | 1.72 | 0.76 | 2.51 | 0.00 | 0 | 0 |

*x = other components, possibly other fluorocarbons

It is believed that the method of the invention provides a means for the conversion of any fluid fluorine- and carbon-containing chemical or substance that is not directly usable, including a fluorocarbon compound having five or more carbon atoms, into useful products, such as TFE, by means of high temperature pyrolysis. In particular, it provides a means for the conversion of liquid fluorocarbon by-products into useful high value fluorine gas products.

The invention claimed is:

1. A method of treating a fluorocarbon feedstock, which method includes
generating, in a high temperature Zone, an electrical arc between at least one cathode and at least one anode;
generating in the high temperature zone and by means of the electrical arc and a plasma gas, a thermal plasma having a tail flame;
introducing a fluorocarbon feedstock in liquid or vapor form and comprising at least one fluorocarbon compound having five or more carbon atoms into the tail flame of the generated thermal plasma; and to form a reactive thermal mixture, the fluorocarbon compound dissociating into at least one fluorocarbon precursor or reactive species having fewer than five carbon atoms; and
cooling the reactive thermal mixture to form, from the fluorocarbon precursor or reactive species, a fluorocarbon product comprising at least one fluorocarbon compound having fewer than five carbon atoms.

2. A method according to claim 1, wherein the plasma gas is an inert gas which acts only as a heat source and to sustain the plasma, and does not react with the fluorocarbon precursor or reactive species.

3. A method according to claim 1, wherein the plasma gas is a reactive gas which, in the thermal plasma and hence in the reactive thermal mixture, dissociates into fluorine containing species and carbon containing species, which, on the cooling of the reactive thermal mixture, react with the fluorocarbon precursor or reactive species to form said fluorocarbon product.

4. A method according to claim 1, wherein the feedstock is a not-directly-usable fluorocarbon product comprising two or more fluorocarbon compounds, with one compound being present in the product as a dominant component so that it constitutes a major proportion of the product.

5. A method according to claim 1, wherein the fluorocarbon feedstock is in liquid form and is introduced into the plasma tail fain; with the plasma gas being fed into the high temperature zone.

6. A method according to claim 5, wherein the feedstock is introduced into the plasma tail flame by feeding the feedstock axially into the plasma rail flame countercurrently to the direction of travel of the plasma tail flame.

7. A method according to claim 5, wherein the cathode and the anode are electrodes of a plasma torch or plasmatron driven by a power supply, with the plasma tail flame forming at the outlet of the torch or plasmatron.

8. A method according to claim 7, wherein the generation of the thermal plasma, the dissociation of the fluorocarbon compound, and the cooling of the reactive thermal mixture are effected in a plasma reactor, to which the plasma torch or plasmatron is mounted, and which has a reaction chamber, with the plasma torch or plasmatron being located at an upper end of the reaction chamber and being downwardly burning so that the plasma tail flame travels downwardly into the reaction chamber.

9. A method according to claim 8, wherein the high temperature zone is provided by a region in and around, and in the immediate vicinity of, the arc of the plasma torch or plasmatron and/or by a region immediately below the plasma torch or plasmatron inside an expansion portion or area of the reaction chamber of the reactor.

10. A method according to claim 9, wherein the expansion of the thermal plasma tail flame, the dissociation of the fluorocarbon compound, and the cooling of the reactive thermal mixture take place in the reaction chamber, with the thermal plasma tail flame expansion and the fluorocarbon compound dissociation being effected in a first zone of the reaction chamber, and the reactive thermal mixture cooling being effected in a second zone of the reaction chamber, with the plasmatron being mounted to the reactor adjacent the first zone of the reaction chamber so that the plasma can be generated and expanded in the first zone of the reaction chamber.

11. A method according to claim 10, wherein the feeding of the plasma gas into the high temperature zone is effected by injecting the plasma gas between the anode and the cathode in such a manner that the thermal plasma forms a vortex in the plasma torch or plasmatron.

12. A method according to claim 10, wherein the cooling of the second zone of the reaction chamber is effected by means of a self-cleaning quench probe.

13. A method according to claim 12, wherein the self cleaning quench probe comprises an outer cylindrical component mounted to the reactor, with the outer cylindrical component providing a central passageway and adapted to cool the hot gas or reactive thermal mixture passing through the passageway; a plurality of circumferentially spaced elongate teeth or scrapers protruding inwardly from the outer component into the passageway; an inner cylindrical component located with clearance inside the outer component, with the inner component also adapted to cool the hot gas or reactive thermal mixture passing along the peripheral gap between the components; a plurality of circumferentially spaced elongate teeth or scrapers protruding outwardly from the inner component into the passageway, with these teeth or scrapers being staggered with respect to the teeth or scrapers on the outer component; and drive means tin driving the one component to oscillate relative to the other component.

14. A method according to claim 1, wherein the fluorocarbon feedstock is in vapour form and is fed into the high temperature zone together with the plasma gas.

* * * * *